(12) United States Patent
Holland et al.

(10) Patent No.: US 11,147,930 B2
(45) Date of Patent: Oct. 19, 2021

(54) SAFETY SYRINGE APPARATUS

(71) Applicant: OWEN MUMFORD LTD, Oxfordshire (GB)

(72) Inventors: Damian Alexander Holland, Oxfordshire (GB); Clive Nicholls, Oxfordshire (GB); Dale Marc Comley, Derbyshire (GB); Lee Thomas Smith, Staffordshire (GB); Joseph David Cowan, Staffordshire (GB)

(73) Assignee: Owen Mumford Limited, Oxford (GB)

( * ) Notice: Subject to any disclaimer, the term of this patent is extended or adjusted under 35 U.S.C. 154(b) by 695 days.

(21) Appl. No.: 16/071,285

(22) PCT Filed: Jan. 19, 2017

(86) PCT No.: PCT/GB2017/050117
§ 371 (c)(1),
(2) Date: Jul. 19, 2018

(87) PCT Pub. No.: WO2017/125734
PCT Pub. Date: Jul. 27, 2017

(65) Prior Publication Data
US 2020/0316311 A1 Oct. 8, 2020

(30) Foreign Application Priority Data
Jan. 19, 2016 (GB) .................................... 1600992

(51) Int. Cl.
*A61M 5/32* (2006.01)
(52) U.S. Cl.
CPC .......... *A61M 5/3271* (2013.01); *A61M 5/326* (2013.01); *A61M 2005/3208* (2013.01)

(58) Field of Classification Search
CPC .......... A61M 5/326; A61M 2005/3152; A61M 2005/3247; A61M 5/31511;
(Continued)

(56) References Cited

U.S. PATENT DOCUMENTS 4,231,368 A * 11/1980 Becker .................... A61M 5/20
604/117
4,840,185 A 6/1989 Hernandez
(Continued)

FOREIGN PATENT DOCUMENTS

| | | |
|---|---|---|
| CA | 2 531 712 A1 | 6/2007 |
| GB | 2529507 A | 2/2016 |

(Continued)

OTHER PUBLICATIONS

Extended European Search Report for Application No. 19153353.8 dated Apr. 24, 2019.
(Continued)

*Primary Examiner* — Rebecca E Eisenberg
(74) *Attorney, Agent, or Firm* — Quarles & Brady LLP

(57) ABSTRACT

An apparatus for use with a syringe to provide a safety syringe, the apparatus including: a sheath deployable for at least partially covering a needle of the syringe; a sheath actuator for deploying the sheath; and a ratioed mechanism linking the sheath and the sheath actuator and configured such that a magnitude of movement of the sheath is greater than a magnitude of movement of the sheath actuator during deployment of the sheath.

6 Claims, 12 Drawing Sheets

(58) Field of Classification Search
CPC ........ A61M 5/3271; A61M 2005/3208; A61M 5/3243; A61M 5/3272; A61M 5/3275; A61M 2005/3265; A61M 5/3257
See application file for complete search history.

(56) References Cited

U.S. PATENT DOCUMENTS

| | | | |
|---|---|---|---|
| 5,318,547 A * | 6/1994 | Altschuler | A61M 5/315 604/198 |
| 7,678,084 B2 * | 3/2010 | Judson | A61M 5/3158 604/187 |
| 8,708,971 B2 | 4/2014 | Segal | |
| 9,943,646 B2 | 4/2018 | Holland | |
| 2003/0233072 A1 | 12/2003 | Hochman | |
| 2007/0073224 A1 | 3/2007 | Dries | |
| 2009/0157060 A1 | 6/2009 | Teague et al. | |
| 2010/0305501 A1 * | 12/2010 | Ratjen | A61M 5/31581 604/82 |
| 2014/0207102 A1 * | 7/2014 | Segal | A61M 5/3157 604/506 |
| 2016/0067417 A1 * | 3/2016 | Bayer | A61M 5/31548 604/208 |
| 2017/0197038 A1 * | 7/2017 | Morlok | A61M 5/3243 |
| 2017/0296753 A1 * | 10/2017 | Rowe | A61M 5/3137 |
| 2020/0188594 A1 * | 6/2020 | Carrel | A61M 5/326 |
| 2021/0112819 A1 * | 4/2021 | Hetherington | A61M 5/3158 |

FOREIGN PATENT DOCUMENTS

| | | |
|---|---|---|
| WO | 2010/127449 A1 | 11/2010 |
| WO | 2012/158135 | 11/2012 |
| WO | 2015/113149 A1 | 8/2015 |
| WO | WO-2015113149 A1 * | 8/2015 ........ A61M 5/31511 |

OTHER PUBLICATIONS

GB Search Report, dated Jul. 14, 2016, from corresponding GB application No. 1600992.0.

International Search Report, dated Jul. 6, 2017, from corresponding PCT application No. PCT/GB2017/050117.

* cited by examiner

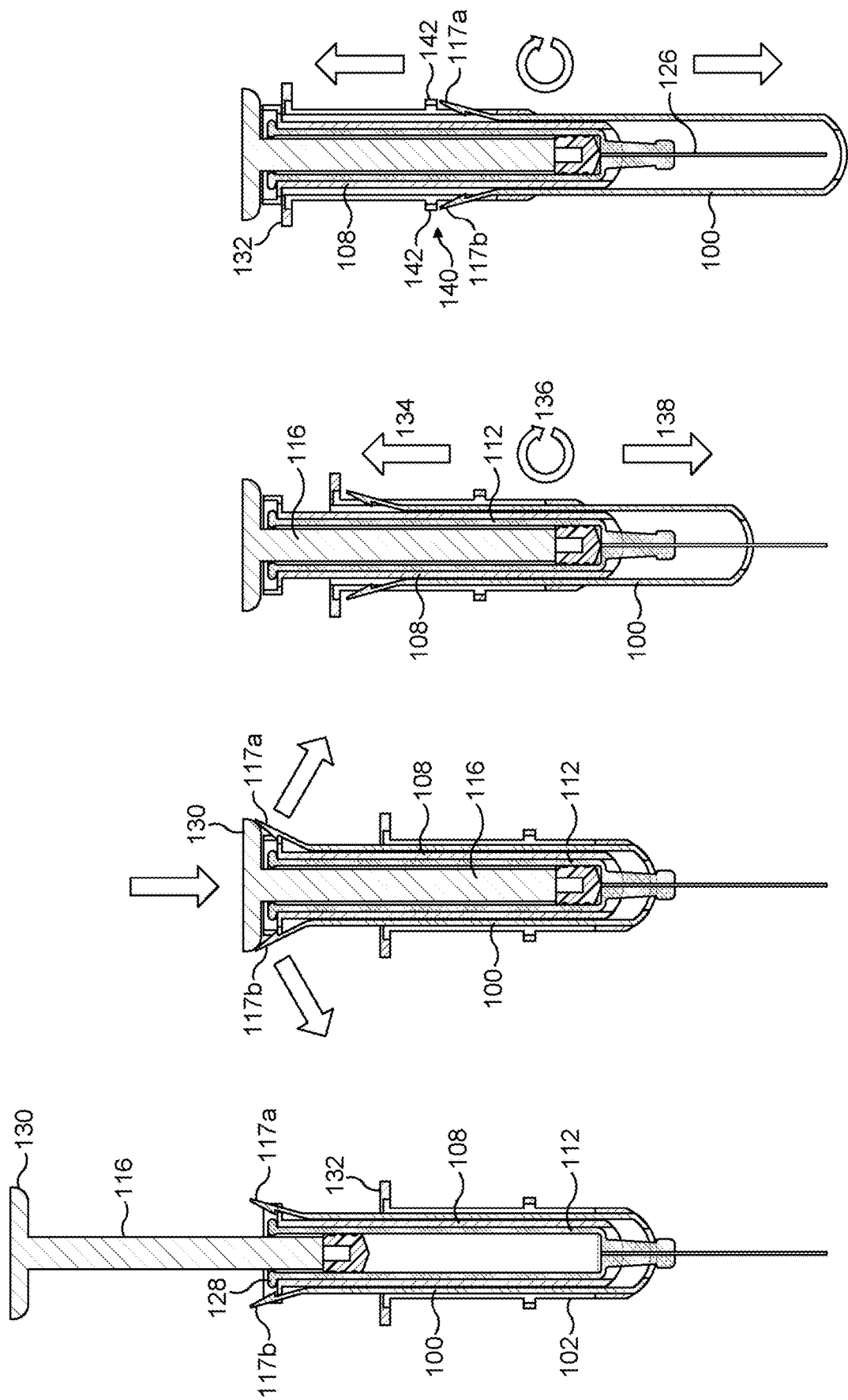

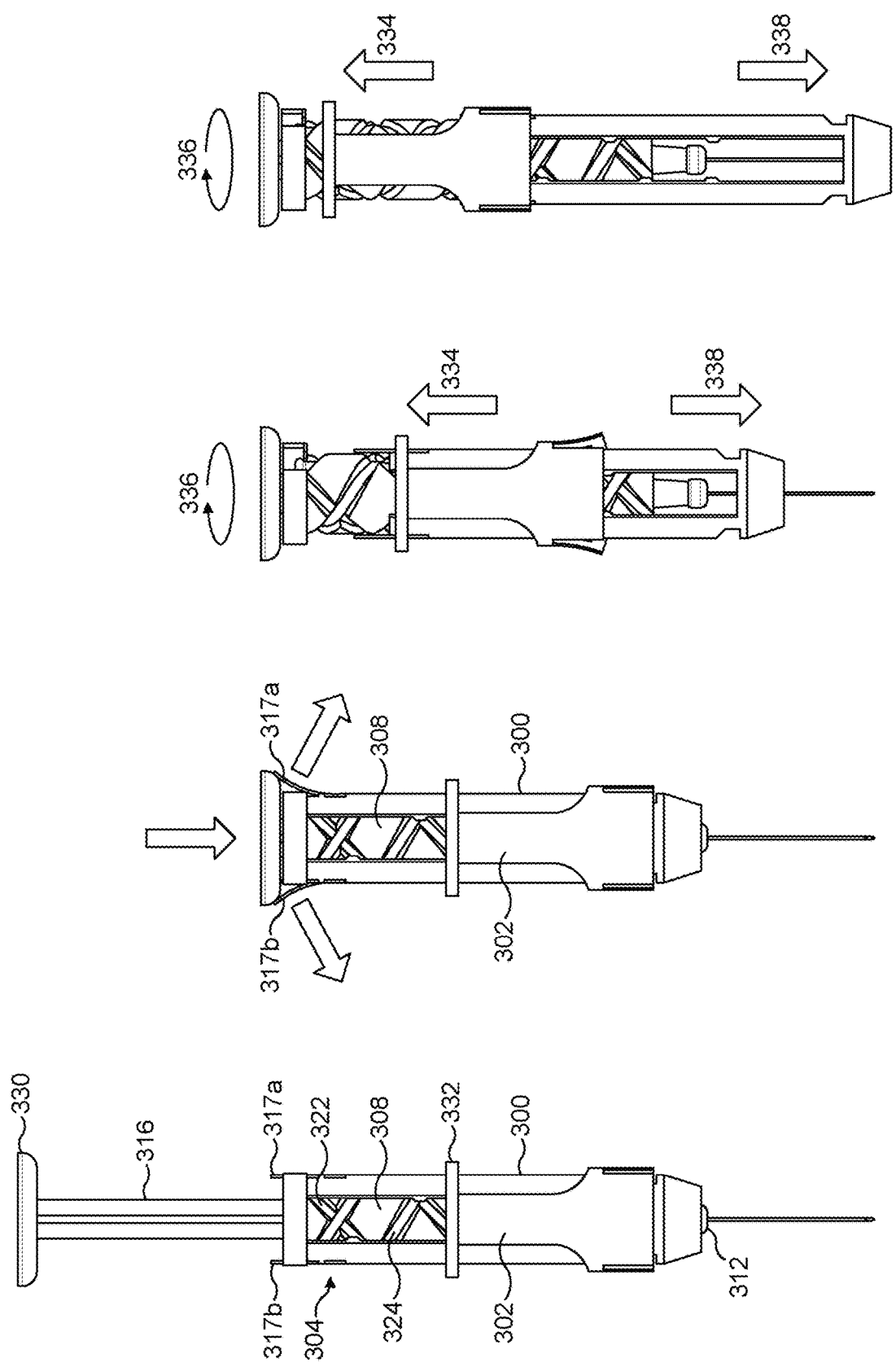

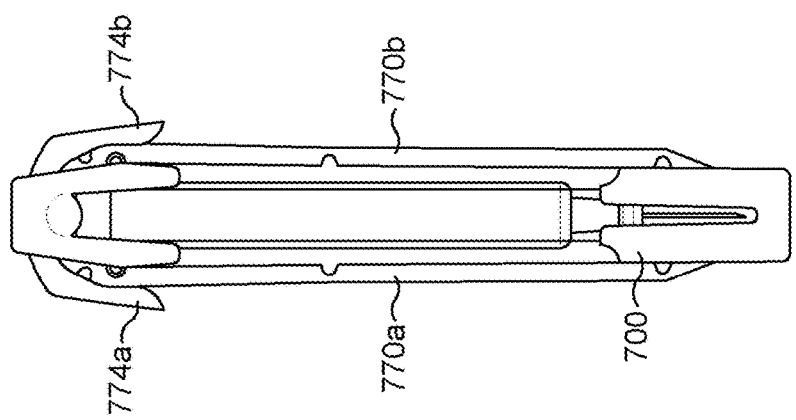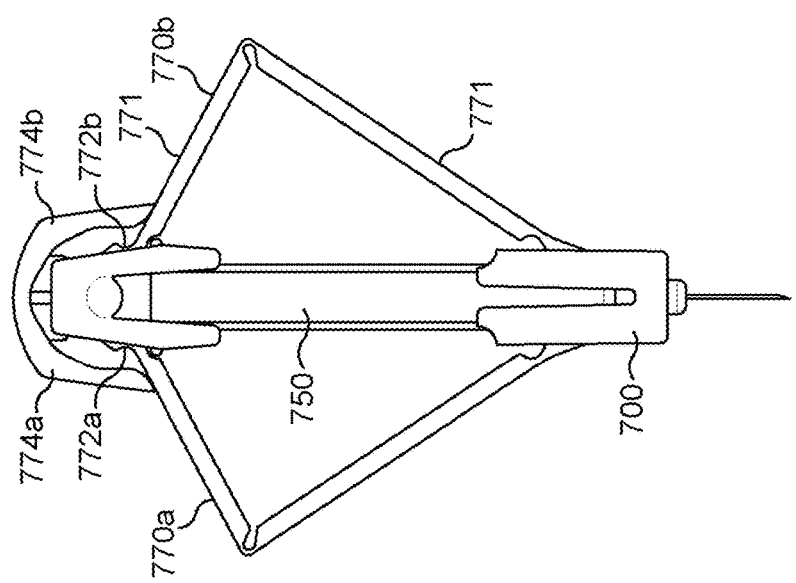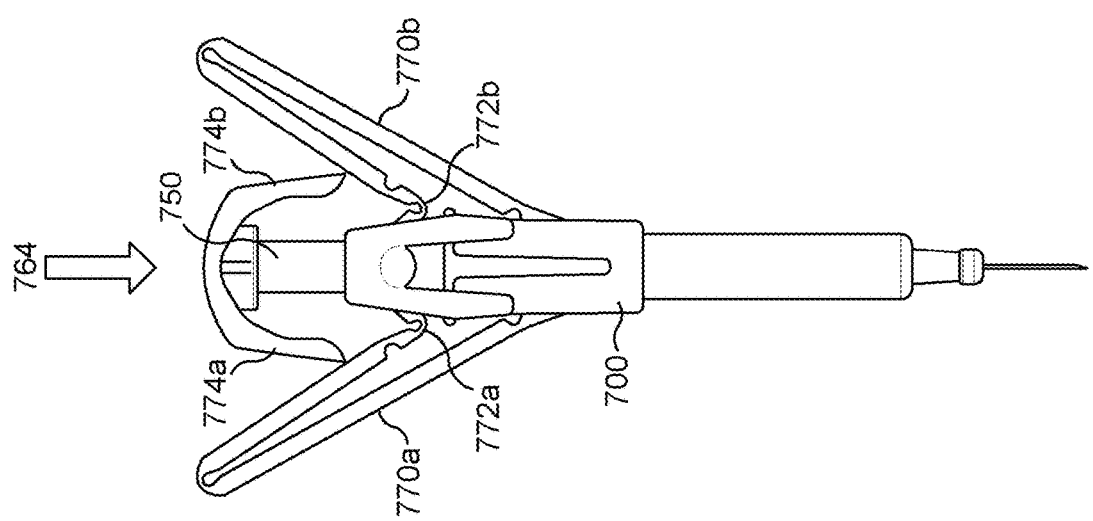

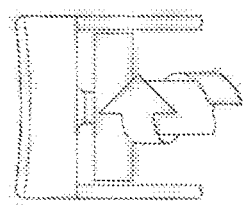
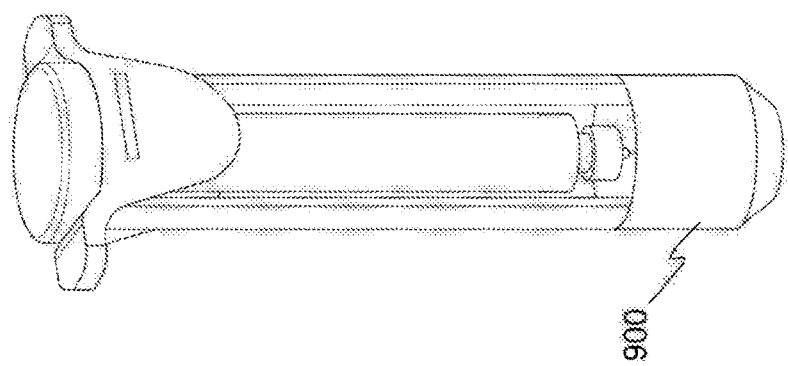
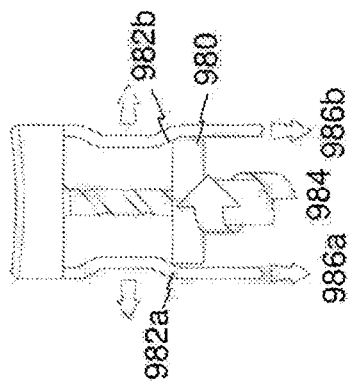
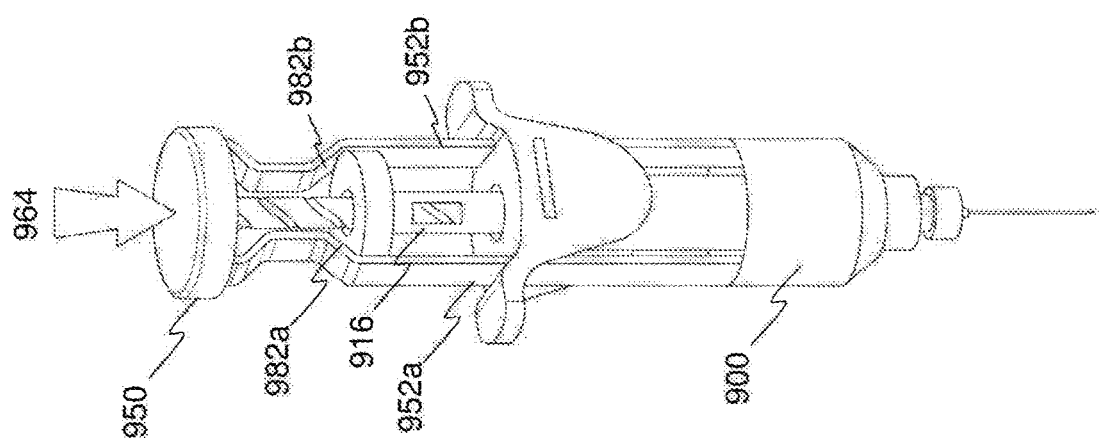
FIG. 10(b')
FIG. 10(b)
FIG. 10(a')
FIG. 10(a)

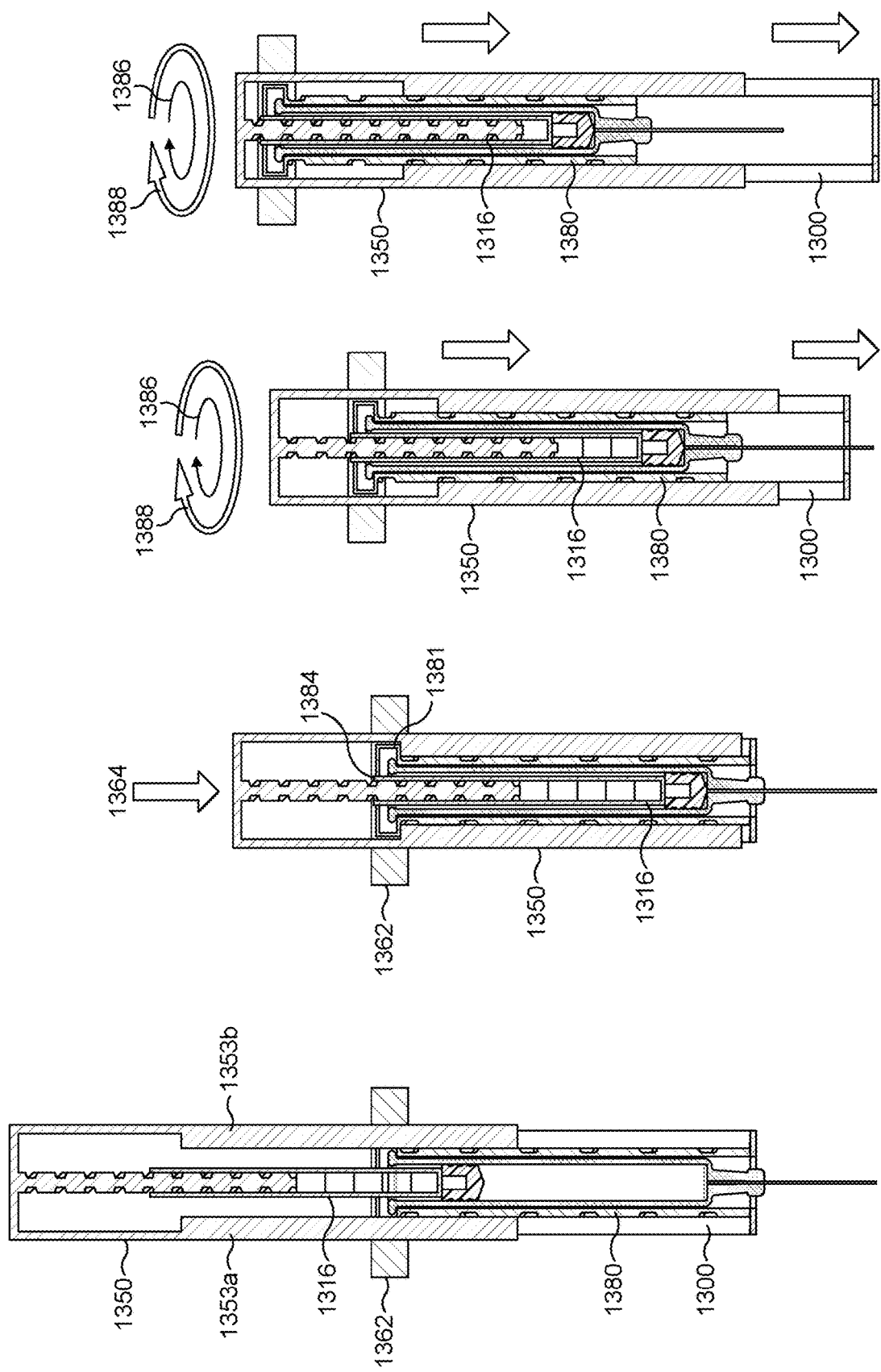

SAFETY SYRINGE APPARATUS

TECHNICAL FIELD

The invention relates to safety syringes and apparatus for fitting to syringes to convert them to safety syringes. In particular embodiments, the invention relates to, but need not be limited to, passive safety syringes and associated apparatus.

BACKGROUND

Broadly, syringes for medical use comprise a barrel having a hypodermic needle at one end and a plunger configured to move within the barrel such that an inward stroke of the plunger causes a substance contained within the barrel to be expelled from an aperture in the needle.

Safety syringes typically include some form of safety mechanism to protect healthcare workers from the hypodermic needle after it has been injected into a patient. Exemplary safety syringes may include a sheath for covering the needle, or may cause the needle to retract within the barrel of the syringe.

Safety syringes may be broadly split into 'active' and 'passive'. Active safety syringes typically require some action by a user of the syringe to engage the safety mechanism. Such action may be taken after removal of the needle from the patient, or may be taken during removal of the needle from the patient. Typically, the action required to engage the safety mechanism is separate from the action required to cause the inward stroke of the plunger. Passive safety syringes typically engage the safety mechanism without any specific action by the user, that is, without any action other than that usually taken to use the syringe.

SUMMARY

The inventors have appreciated that a safety syringe may comprise a spring-loaded safety mechanism that may be engaged by a healthcare worker after, and separate to, the inward stroke of the plunger. That is, the healthcare worker takes a separate action to engage the spring-loaded mechanism. The spring force urges a surface against the skin of the patient, thereby extracting the needle and simultaneously engaging a safety mechanism, such as a sheath. Such devices are prone to misuse as healthcare workers are known to remove the needle from the patient before engaging the safety mechanism. This exposes the healthcare worker to the needle after use and the spring-loaded action of the safety mechanism may lead to blood splatter from the needle.

Other known safety syringes require the needle to be removed from the patient before the safety mechanism may be engaged. This exposes the healthcare worker to the needle after use.

According to the invention in an aspect, there is provided an apparatus for use with a syringe to provide a safety syringe, the apparatus comprising: a sheath deployable for at least partially covering a needle of the syringe; a sheath actuator for deploying the sheath; and a ratioed mechanism linking the sheath and the sheath actuator and configured such that a magnitude of movement of the sheath is greater than a magnitude of movement of the sheath actuator during deployment of the sheath.

Optionally, the sheath actuator is operable on in-line movement thereof.

Optionally, the sheath actuator comprises a plunger and a handle portion configured for deploying the sheath by relative movement between the plunger and the handle portion.

Optionally, the ratioed mechanism comprises a rack and pinion arrangement.

Optionally, the ratioed mechanism comprises a pinion engaged with a first rack connected to the sheath actuator and a second rack connected to the sheath.

Optionally, the pinion comprises a first set of teeth engaged with the first rack and a second set of teeth engaged with the second rack, and wherein the first set of teeth has a smaller radius than the second set of teeth.

Optionally, the ratioed mechanism comprises a helical guide configured to be rotatable by the sheath actuator and to engage with a corresponding feature of the sheath for deployment thereof.

Optionally, the helical guide is located on a mount, rotatable by the sheath actuator with respect to the sheath.

Optionally, the apparatus comprises a further helical guide configured to engage with a corresponding feature on the sheath actuator for rotation of the helical guide.

Optionally, the plunger comprises a safety plunger coupled to a syringe plunger, the safety plunger being configured decouple from the syringe plunger at a point on a stroke of the syringe plunger, and wherein the further helical guide is located on the safety plunger and/or the syringe plunger for relative rotation therebetween after decoupling.

Optionally, the further helical guide is located on the mount.

Optionally, the helical guide and/or further helical guide comprise channels and the corresponding features on the sheath actuator and the sheath comprise lugs and/or a corresponding helical protrusion.

Optionally, the angle of the helical guide is greater than the angle of the further helical guide.

Optionally, the helical guides are in opposed directions.

Optionally, the sheath is configured to be in fixed relation to a barrel of the syringe, and is further configured to be released from the fixed relation at a point on a stroke of a plunger of the syringe.

Optionally, the sheath comprises fixings configured to fix the sheath in relation to the barrel, and wherein the fixings are further configured to be released on contact with a portion of the plunger.

Optionally, the plunger comprises a syringe plunger and the sheath actuator comprises a safety plunger coupled to the syringe plunger, the safety plunger being configured to decouple from the syringe plunger at a point on a stroke of the syringe plunger, and wherein movement of the safety plunger after decoupling actuates deployment of the sheath.

Optionally, the safety plunger comprises one or more legs for coupling to the sheath, and wherein one or more the legs are configured to provide the ratioed mechanism.

Optionally, an extension of the one or more legs is configured to be increasable following decoupling of the safety plunger and the syringe plunger.

Optionally, the one or more legs are bendable and are configured to be straightened such that the extension of the one or more legs is increased.

Optionally, the one or more legs are hinged for allowing them to be straightened.

Optionally, a lateral extent of the legs is limited after decoupling for allowing them to be straightened.

Optionally, the one or more legs are configured to pass a guide for constraining their lateral extent.

Optionally, the guide comprises an aperture fixed in relation to the syringe.

Optionally, the one or more bendable legs are bent to provide a reaction surface configured to engage a straightening member during a stroke of the safety plunger.

Optionally, the sheath actuator further comprises one or more lever arms coupled to the sheath to cause deployment thereof.

Optionally, the one or more lever arms are configured to provide the ratioed mechanism.

Optionally, the one or more lever arms are operable on movement of the safety plunger.

Optionally, first ends of the one or more lever arms are rotatable at a position fixed with respect to the syringe or the safety plunger and wherein second ends of the one or more lever arms are connected to the sheath, and wherein the sheath actuator further comprises a rotator fixed with respect to the other of the syringe and the safety plunger and configured to rotate the first end of the one or more lever arms for deployment of the sheath.

Optionally, the one or more lever arms comprise a plurality of hinged sections.

Optionally, the one or more lever arms are bendable and are configured to be at least partially straightened for deployment of the sheath.

Optionally, the apparatus according to any preceding claim, further comprising a lock configured to retain the sheath in a position at least partially covering a needle of the syringe.

Optionally, the lock comprises a first locking feature formed on the sheath and configured to engage with a second locking feature formed on the sheath actuator.

According to the invention in another aspect, there is provided a safety syringe comprising a syringe and any apparatus for use with a syringe to provide a safety syringe disclosed herein.

According to the invention in another aspect, there is provided a kit of parts comprising: a sheath; a sheath actuator for deploying the sheath; and a ratioed mechanism, wherein, when fitted to a syringe, the sheath is deployable for at least partially covering a needle of the syringe and the ratioed mechanism links the sheath and the sheath actuator and is configured such that a magnitude of movement of the sheath is greater than a magnitude of movement of the sheath actuator during deployment of the sheath.

BRIEF DESCRIPTION OF DRAWINGS

FIGS. 2a-d show stages of operation of an exemplary apparatus fitted to a syringe for providing a safety syringe;

FIGS. 4a-d show stages of operation of an exemplary apparatus fitted to a syringe for providing a safety syringe;

FIGS. 8a-c show stages of operation of an exemplary apparatus fitted to a syringe for providing a safety syringe;

FIGS. 10a, a', b and b' show stages of operation of an exemplary apparatus fitted to a syringe for providing a safety syringe;

FIGS. 14a-d show stages of operation of an exemplary apparatus fitted to a syringe for providing a safety syringe.

DETAILED DESCRIPTION

Generally, disclosed herein are safety syringes and apparatus for providing safety syringes, in which a sheath is extended along a length of a barrel of a syringe to cover at least partially a needle of the syringe. The sheath may be urged over the needle by a force applied by the user, typically during normal use of the syringe. A sheath actuator moves to deploy the sheath and the movement of the sheath is ratioed with respect to movement of the sheath actuator such that a magnitude of movement of the sheath is greater than a magnitude of movement of the sheath actuator. Further, the sheath actuator may be configured to cause deployment of the sheath from in-line movement thereof. The term "in-line" is used to encompass longitudinal movement aligned with a longitudinal axis of the safety syringe. In-line movement may be caused by a normal action of a user using a syringe.

It is noted that, although the apparatus described relate to syringes including a barrel, needle and syringe plunger, exemplary apparatus may also relate to an apparatus for fitting to a syringe. That is, exemplary apparatus need not include the barrel, needle and/or syringe plunger.

As used herein, the term "syringe plunger" encompasses a plunger that has an element configured to move within a barrel of a syringe to dispense a substance contained within the barrel.

Further, exemplary apparatus are described herein and relate to relative movement between various features of the apparatus. It should be understood that it is relative movement that is used to operate some of the features of the apparatus. For example, a sheath actuator may be moved and the syringe remain stationary in order to deploy a sheath, but the same effect may be achieved by movement of a syringe if the sheath actuator remains stationary. The descriptions provided herein assume that the syringe remains stationary.

Figure 1:
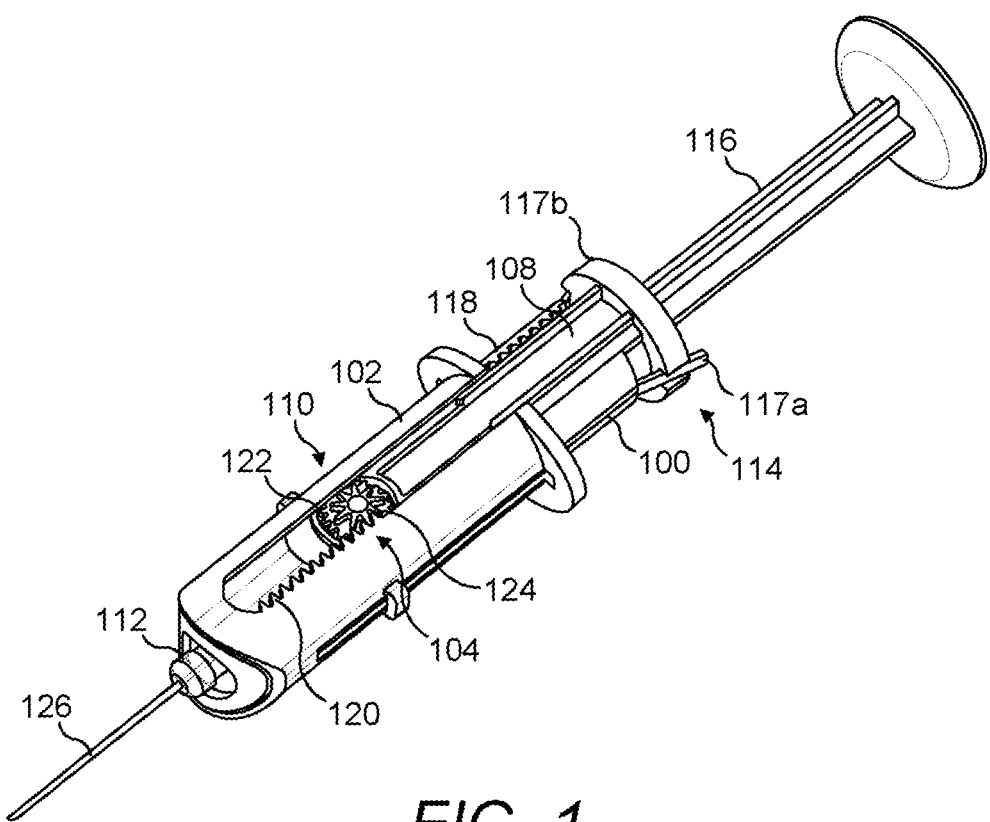
FIG. 1 is a perspective view of an exemplary apparatus fitted to a syringe for providing a safety syringe.

FIG. 1 shows an exemplary apparatus for fitting to a syringe for providing a safety syringe. The apparatus is shown fitted to a syringe in FIG. 1. The apparatus comprises a sheath 100 and a sheath actuator 102. A ratioed mechanism 104 links the sheath 100 and the sheath actuator 102 such that movement of the sheath actuator 102 causes movement of the sheath 100. In the exemplary apparatus of FIG. 1, the ratioed mechanism 104 comprises The ratioed mechanism 104 of the exemplary apparatus of FIG. 1 is configured to cause movement of the sheath 100 in an opposite direction to the movement of the sheath actuator 102. Further, the ratioed mechanism 104 is configured such that the movement of the sheath 100 is greater than the corresponding movement of the sheath actuator 102.

The ratioed mechanism 104 comprises a mount 108, to which a pinion 110 is rotatably connected. The mount 108 is fixed to a barrel 112 of the syringe when the apparatus is fitted to the syringe. The sheath 100 and the sheath actuator 102 are configured to be slidable relative to the mount 108. Specifically, the sheath 100 is arranged to slide on an outer surface of the mount 108 and the sheath actuator 102 is configured to slide on an outer surface of the sheath 100. The sheath 100 has a fixing 114 that is configured to hold the sheath 100 in fixed relation to the mount 108 (and/or the barrel 112) until such time as it is released at a point on the stroke of a syringe plunger 116 of the syringe. This is explained in greater detail below. The stroke of the syringe plunger 116 encompasses the inward and outward movement of the syringe plunger 116 within the syringe barrel 112. The fixings 114 comprise two lugs 117a, 117b configured to engage with a lip (shown in FIGS. 2a-d) at a syringe plunger opening of the barrel 112 or with a lip of the mount 108.

The ratioed mechanism 104 further comprises a first rack 118 formed on the sheath 100 and a second rack 120 formed on the sheath actuator 102. The first and second racks 118, 120 are engaged with the pinion 110. The pinion 110 comprises a first set of teeth 122 engaged with the first rack 118 and a second set of teeth 124 engaged with the second rack 120. The second set of teeth 124 has a greater radius than the first set of teeth 122, such that movement of the sheath actuator 102 causes a greater magnitude of movement of the sheath 100.

The sheath 100 is extendable over at least part of the length of the apparatus such that it covers a needle 126 of the syringe after use thereof.

FIGS. 2a-d show a section through the apparatus and syringe of FIG. 1 at various stages of the operation.

Referring to FIG. 2a, the apparatus is in an unused condition. The mount 108 is fitted to the lip 128 at the syringe plunger aperture of the barrel 112. The lugs 117a-b of the fixing 114 are engaged with a lip of the mount 108, such that the sheath 100 is in a fixed relation to the mount 108 and the barrel 112. The syringe plunger 116 is at an outermost point on its stroke.

A user depresses the syringe plunger 116, which may be done by placing the thumb on a syringe plunger head 130 and the index and middle fingers against a finger grip 132 of the sheath actuator 102 and applying a relative pressure between the thumb and fingers. This concept of operation is typical in syringes. Because the sheath 100 is fixed in relation to the mount 108 and barrel 112, the sheath actuator 102 is prevented from moving, as it is linked to the sheath 100 by the ratioed mechanism 104 (not shown in FIGS. 2a-d, as they are sections). The second rack 124 is prevented from rotating the pinion 110 because the first rack 122 is fixed.

Referring to FIG. 2b, when the syringe plunger 116 reaches a predefined point on its inward stroke (the end of the inward stroke in the exemplary apparatus of FIGS. 1 & 2a-d), the syringe plunger head 130 meets the lugs 117a-b and displaces them out of engagement with the lip of the mount 108. The fixing 114 is therefore released and the sheath 100 is no longer in fixed relation to the mount 108 and/or barrel 112. As such, the ratioed mechanism 104 is now free to move. It is noted that other forms of decoupling of the sheath actuator 102 are possible. Exemplary decoupling means are configured to retain the sheath actuator 102 in position until the plunger reaches a predefined point on the inward stroke.

Referring to FIG. 2c, continued movement of the syringe plunger 116 results in movement of the sheath actuator 102 relative to the mount 108 and/or the barrel 112. Movement of the sheath actuator 102 is represented by arrow 134. This causes rotation of the pinion 110, which is represented by arrow 136. This in turn causes movement of the sheath 100, which is represented by arrow 138. Because of the ratioed relationship between the sets of teeth on the pinion 110, the magnitude of the movement of the sheath 100 is greater than the magnitude of the movement of the sheath actuator 102.

Referring to FIG. 2d, the sheath actuator 102 has moved to a limit of movement, at which the finger grip 132 abuts the lip of the mount 108. The sheath 100 is extended, such that it covers the needle 126. Further, a lock 140 is engaged, such that the sheath may not be moved out of its extended position. The lock 140 of the exemplary apparatus of FIGS. 1 and 2a-d locks the sheath 100 in relation to the sheath actuator 102. Specifically, the lugs 117a-b are biased outwardly and therefore extend through apertures in the sheath actuator 102 such that they are restrained by locking surface 142 on the sheath actuator 102.

Figure 3:
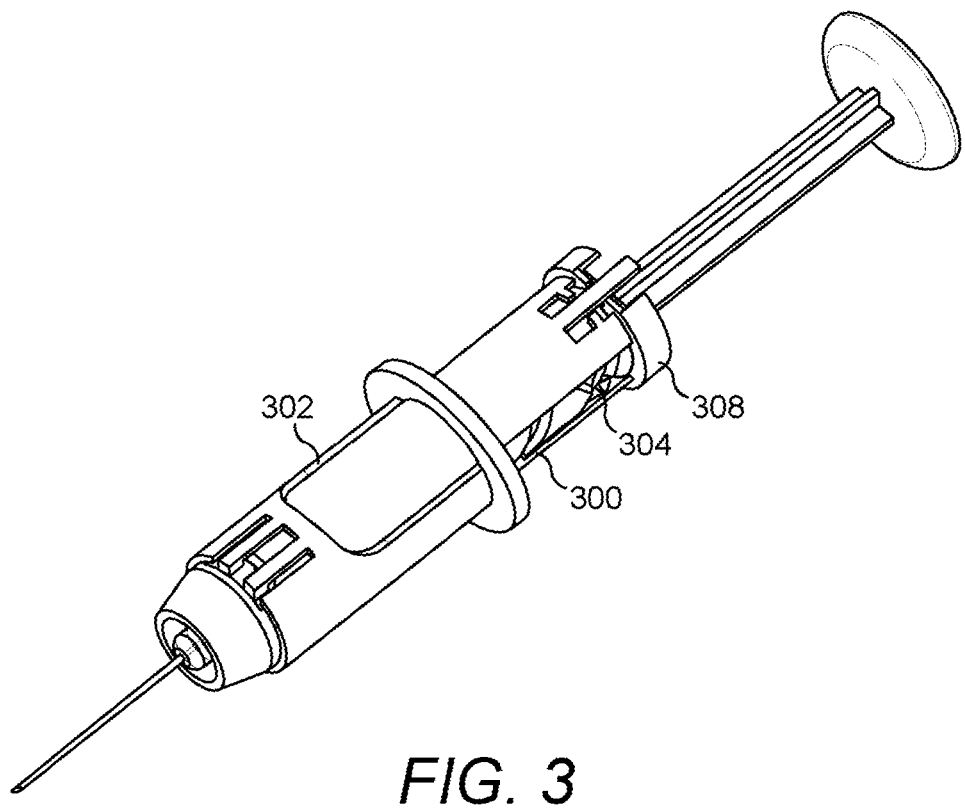
FIG. 3 is a perspective view of an exemplary apparatus fitted to a syringe for providing a safety syringe.

FIG. 3 shows an exemplary apparatus fitted to a syringe. Many of the features of the apparatus of FIG. 3 are the same or similar to corresponding features of the apparatus of FIG. 1 and may have the same or a similar purpose. As such, these features are not described again in detail here. Similar reference numerals may be used for similar features, except prefixed by a "3".

A ratioed mechanism 304 of the exemplary apparatus of FIG. 3 comprises a helical guide 322 and a further helical guide 324, which are best shown in FIGS. 4a-d. The helical guide 322 is configured to interact with a corresponding feature on the sheath 300 and the further helical guide 324 is configured to interact with corresponding features on the sheath actuator 302. In the exemplary apparatus of FIG. 3, the helical guides 322, 324 comprise channels formed in the mount 308 and the corresponding features of the sheath 300 and the sheath actuator 302 comprises guiding lugs configured to travel within the channels. The mount is rotatable with respect to the sheath 300 and the sheath actuator 302 and may also be rotatable with respect to the barrel of the syringe.

The helical guides 322, 324 need not form a full 360 degree revolution around the apparatus and may form a partial revolution. In this sense, the helical guides 322, 324 need not be a full helix (i.e. greater than a 360 degree revolution), but may be a curved guide formed around an outer of the mount 308. The helical guides 322, 324 are angled such that the sheath 300 and sheath actuator 302 respectively move along a length of the apparatus as the guiding lugs travel in the channels. The angle of the helical guides 322, 324 refers to the steepness of the gradient of the helical guide, which controls the amount of linear motion translated by the guiding lugs from a given amount of rotational motion. The angle of each of the helical guides 322, 324 is different. The helical guides are in opposed directions, such that movement of the sheath actuator 302 in one direction results in movement of the sheath 300 in an opposite direction.

FIGS. 4a-d show a number of side views of the exemplary apparatus of FIG. 3 at various stages of operation. The mount 308 is connected to the barrel 312 and the sheath 300 is connected to the mount 308 by the lugs 317a-b. The helical guides 322, 324 can be seen to be channels formed in the mount 308. The sheath actuator 302 and the sheath 300 are not rotatable about the barrel 312. The mount 308 is configured to be rotatable with respect to the sheath 300 and the sheath actuator 302.

A user begins to operate the syringe by applying relative force between the finger grip 332 and the head 330 of the syringe plunger 316 to bring them together, similar to the process described in relation to FIGS. 2a-d. Because the sheath 300 is in a fixed relationship with the mount 308, the mount 308 cannot rotate and so guiding lugs of the sheath actuator 302 cannot travel in the further helical guide 324.

Referring to FIG. 4b, when the syringe plunger 316 has reached the end of its stroke, the syringe plunger head 330 contacts the lugs 317a-b and displaces them laterally such that they are no longer engaged with the mount 308. The mount 308 is now free to rotate with respect to the sheath 300 and the sheath actuator 302. As noted above, other forms of decoupling of the sheath actuator 302 are possible. Generally, exemplary decoupling means are configured to retain the sheath actuator 302 in position until the plunger reaches a predefined point on the inward stroke. After the predefined point, the sheath actuator 302 is moveable to deploy the sheath 300.

As shown in FIG. 4c, movement of the sheath actuator 302 relative to the syringe plunger 316 (shown by arrow 334) after this decoupling results in the guiding lugs of the sheath actuator 302 travelling within the further helical guide 324 in the direction shown by arrow 334, which in turn rotates the mount 308 (shown by arrow 336) and forces the sheath 300 to move in the opposite direction (shown by arrow 338) because of the interaction of the guiding lug on the sheath 300 and the helical guide 322.

As shown in FIG. 4d, the movement of the sheath 300 is greater than the movement of the sheath actuator 302.

Figure 5:
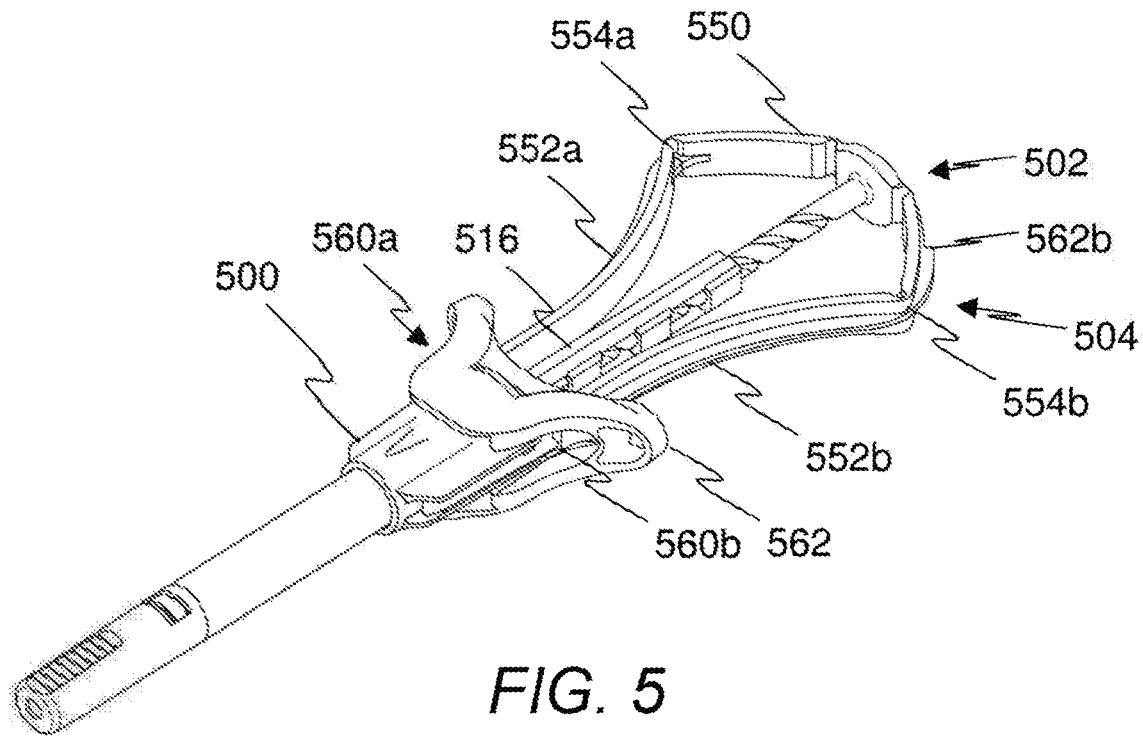
FIG. 5 is a perspective view of an exemplary apparatus fitted to a syringe for providing a safety syringe.

FIG. 5 shows an exemplary safety syringe apparatus fitted to a syringe. Some of the features of the apparatus of FIG. 5 are the same or similar to corresponding features of the apparatus of FIGS. 1 and 3, and may have the same or a similar purpose. As such, these features are not described again in detail here. Similar reference numerals may be used for similar features, except prefixed by a "5".

The exemplary apparatus of FIG. 5 comprises a sheath 500 and a sheath actuator 502. The sheath actuator 502 comprises a safety plunger 550 that is coupled to a syringe plunger 516. The safety plunger 550 is configured to decouple from the syringe plunger 516 at a point on the stroke of the syringe plunger 316. Typically, the point on the stroke is the end of the stroke when all of the substance within the barrel has been dispensed. After decoupling, further movement of the safety plunger 550 causes deployment of the sheath 500.

As used herein, the term "safety plunger" encompasses a feature of exemplary apparatus that is configured to deploy a sheath. Safety plungers may deploy the sheath on a normal syringe operating action of the user, that is, the user may operate the apparatus as normal and the syringe plunger will deploy the sheath under the applied force.

The sheath actuator is coupled to the sheath by legs 552a-b. The coupling is direct in that movement of the sheath actuator 502 causes movement of the sheath 500, but the coupling is also by way of a ratioed mechanism 504 provided by the legs 552a-b. That is, the legs 552a-b provide the ratioed mechanism 504. The legs 552a-b are bent and are configured to be straightened such that an overall extension of the legs 552a-b is increased. That is, when the legs 552a-b are straightened then the straight line distance between the top of the legs 552a-b and the bottom of the legs 552a-b is increased compared to when they are bent. It is noted that straightening of the legs 552a-b need not be a full straightening in order to achieve the desired effect. In exemplary apparatus, a partial straightening may suffice.

Figure 5A:
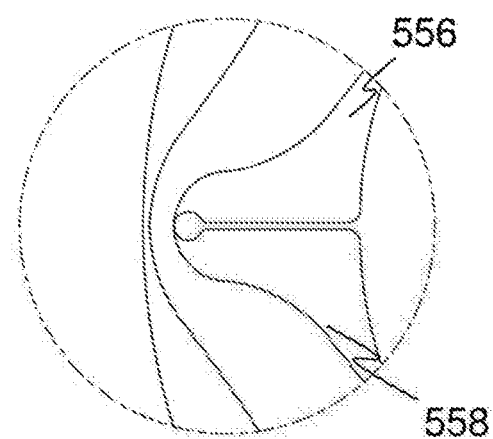
FIG. 5a is an enlarged view of a hinge in a leg of an exemplary apparatus.

The legs 552a-b have hinges 554a-b that allow the legs 552a-b to be straightened. FIG. 5a shows a close up view of a hinge 554a-b. The hinge 554a-b comprises hinge restrictors in the exemplary form of fillets 556, 558. The fillets 556, 558 are configured to interact to prevent the hinge 554a-b operating in one direction. In FIGS. 5 and 5a, the fillets 556, 558 prevent closing of the hinge 554a-b beyond a point because they will interfere with each other. The legs 552a-b are able to straighten but not to become more bent.

The legs 552a-b extend to guides 560a-b that are fixed in relation to the syringe. The guides are configured to limit the lateral extent of the legs 552a-b (e.g. due to the bending as they pass the respective guide 560a-b. In the exemplary apparatus of FIG. 5, the guides 560a-b comprise apertures. The apertures are located in a handle portion 562 fitted to the syringe.

The safety plunger 550 is coupled to the syringe plunger 516 at a start point of the stroke. In the exemplary apparatus of FIG. 5, the coupling is provided by a combination of a threaded portion of the safety plunger 550 and a keyed entry of the syringe plunger 516 into the barrel of the syringe. The syringe plunger 516 is prevented from rotating along at least part of its stroke and in the exemplary apparatus of FIG. 5, the rotation is prevented by a non-circular cross sectional shape of the syringe plunger 516 interacting with a corresponding aperture at the entrance to the barrel. The syringe plunger 516 is configured to be rotatable at a point on the stroke, such that the safety plunger 550 and the syringe plunger become decoupled, that is, linear motion of the safety plunger 550 need not result in linear motion of the syringe plunger 516. Each leg 552a-b also comprises a locking feature 562a-b comprising a ramped section configured to pass through the apertures of the guides 560a-b and a locking surface configured to snap into a position to engage with an underside of the apertures to prevent retraction of the safety plunger 550 and syringe plunger 516.

Figure 6A:
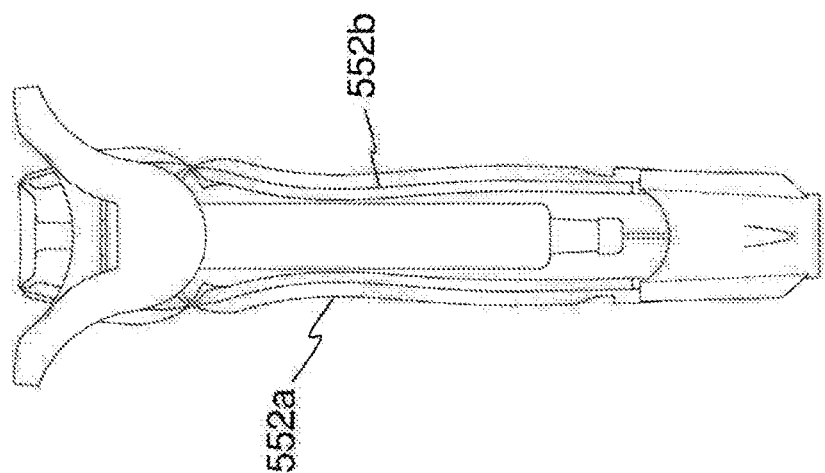
FIGS. 6a-c show stages of operation of an exemplary apparatus fitted to a syringe for providing a safety syringe.

FIG. 6a shows the apparatus of FIG. 5 at the start of the stroke of the syringe plunger 516. As a force is applied to the safety plunger 550 in the direction of the arrow 564, the safety plunger 550 and the syringe plunger 516 are coupled and the syringe plunger therefore moves within the barrel of the syringe. The legs 552a-b are prevented from bending further by the fillets 556, 558 on the hinges 554a-b. The legs 552a-b pass through the guides 560a-b (not shown in FIGS. 6a-c) and the sheath 500 moves towards the needle.

Figure 6B:
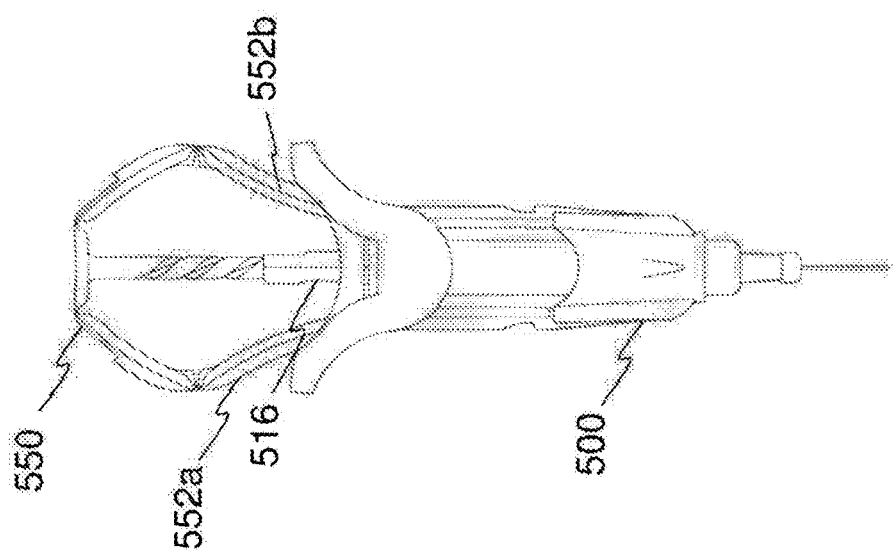

Referring to FIG. 6b, as the bent portions of the legs 552a-b pass through the guides 560a-b they are forced to straighten as their lateral extension is constrained by the guides 560a-b. The straightening of the legs 552a-b increases their extension down the length of the syringe and results in greater movement of the sheath 500 for a corresponding movement of the safety plunger 550.

After the syringe plunger 516 passes the keyed aperture at the opening of the barrel, it is free to rotate and becomes decoupled from the safety plunger 550. It is noted that other forms of decoupling are possible. Further movement of the safety plunger 550 causes rotation of the syringe plunger 516 due to the threaded portion of the safety plunger interacting with a corresponding threaded portion within the syringe plunger 516.

Figure 6C:
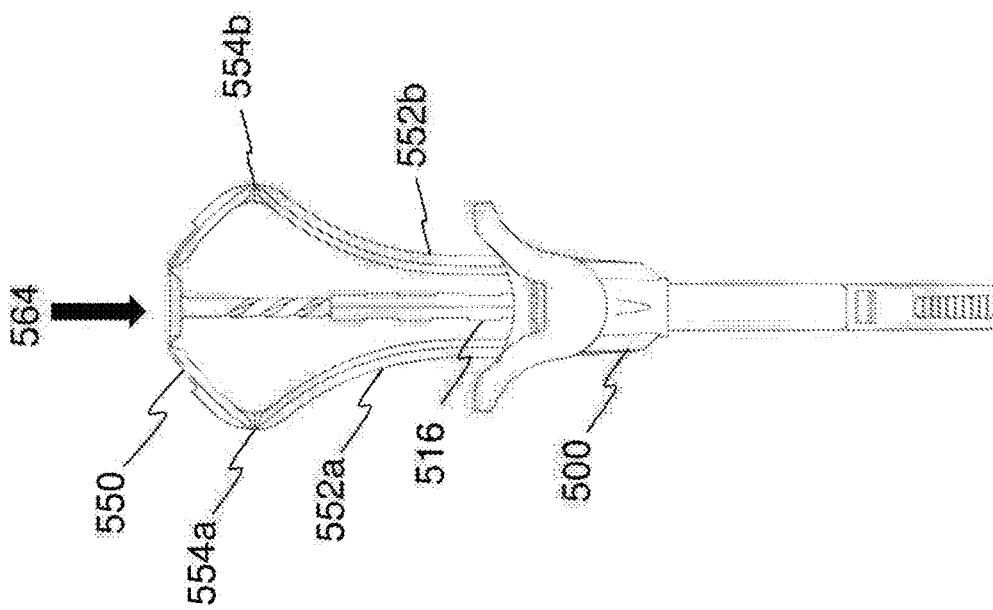

As shown in FIG. 6c, the legs 552a-b are therefore passed further through the guides 560a-b and are straightened further, resulting in increased extension of the sheath 500. After the locking features 562a-b pass through the guides 560a-b the safety plunger 550 may not be extracted and the sheath 500 is locked in a position covering the needle.

Figure 7:
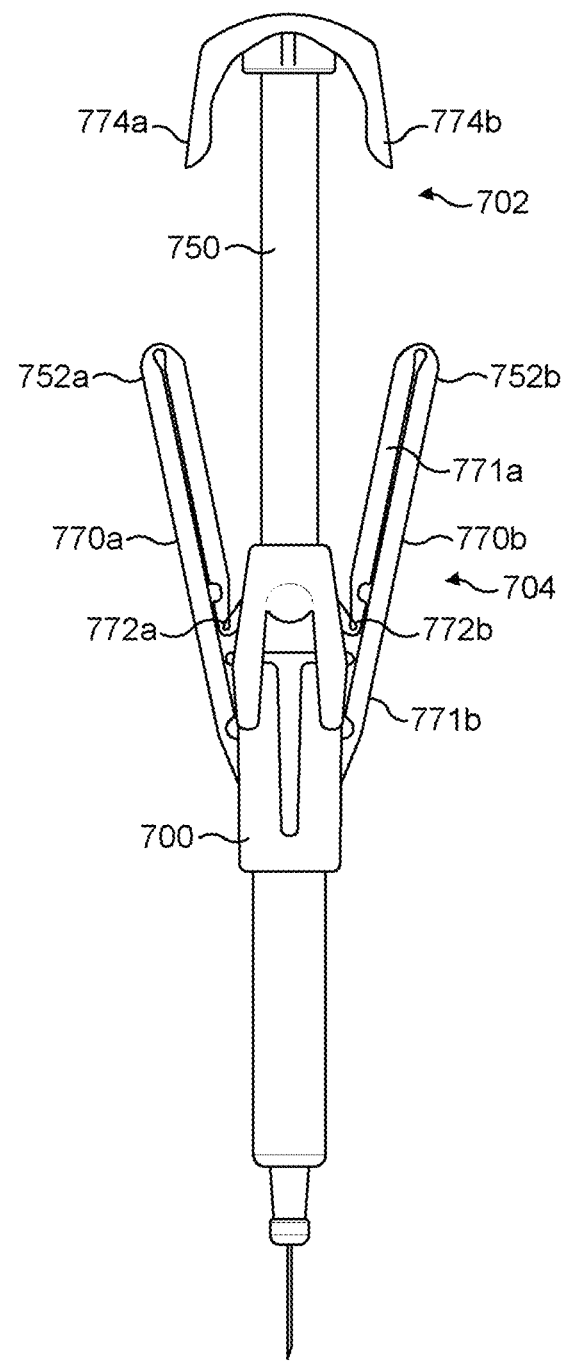
FIG. 7 is a perspective view of an exemplary apparatus fitted to a syringe for providing a safety syringe.

FIG. 7 shows an exemplary safety syringe apparatus fitted to a syringe. Some of the features of the apparatus of FIG. 7 are the same or similar to corresponding features of the apparatus of any of FIGS. 1, 3 and 5 and may have the same or a similar purpose. As such, these features are not described again in detail here. Similar reference numerals may be used for similar features, except prefixed by a "7".

The exemplary apparatus of FIG. 7 comprises a sheath 700 and a sheath actuator 702. The sheath actuator 702 comprises a plunger 750 that in the exemplary apparatus of FIG. 7 is a syringe plunger, but in other exemplary apparatus may be a safety plunger coupled to a syringe plunger and configured to decouple from the syringe plunger at a point on the inward stroke. There are a number of ways that such decoupling may occur and one way is as described with reference to FIGS. 5 and 6a-c above. The sheath actuator 702 also comprises lever arms 770a-b and rotators 774a-b. The lever arms 770a-b are connected between the sheath 700 and a point fixed in relation to the barrel of the syringe. The rotators 774a-b comprise projections from an underside of a plunger head and are arranged to interact with the lever arms on depression of the plunger 750, as explained below. An inward stroke of the plunger 750 does not result in movement of the sheath 700 until rotators 774a-b on the safety plunger 750 engage with lever arms 770a-b.

The lever arms 770a-b provide a ratioed mechanism 704 for deployment of the sheath 700. The lever arms 770a-b are bendable and may be straightened so as to increase the extension of the sheath 700 during deployment. In particular, first ends of the lever arms 770a-b are rotatable at points 772a-b that are fixed with respect to the syringe and/or are moveable relative to the plunger 750. In the exemplary apparatus of FIG. 7, the first ends of the lever arms 770a-b are rotatably connected to a handle portion of the safety syringe. Second ends of the lever arms 770a-b are connected to the sheath 700. The lever arms 770a-b comprise a plurality of hinged sections 771a-b (referenced on one lever arm 770b only in FIG. 7).

The plunger 750, which forms part of the sheath actuator 702, comprises rotators 774a-b that are configured to rotate the lever arms 770a-b at a point on the inward stroke of the plunger 750. In the exemplary apparatus of FIG. 7, the rotators 774a-b comprise projections from the head of the safety plunger 750 configured to engage the lever arms 770a-b for rotating them about the points 772a-b.

Referring to FIG. 8a, as a user begins to apply a force to a head of the plunger 750 as represented by arrow 764. The plunger 750 moves on its inward stroke and causes a substance in the barrel to be forced from the needle of the syringe. At a point on the inward stroke, the rotators 774a-b contact the lever arms 770a-b, which are then rotated about the points 772a-b.

This motion continues, as shown in FIG. 8b and the rotation of the lever arms 770a-b causes linear extension of the sheath 700 along the barrel of the syringe. The linear motion of the sheath 700 is greater than the linear movement of the plunger 750 because of the length of the first hinged section 771a of the lever arms 770a-b. As the hinged portions 771a-b of the lever arms 770a-b are straightened and longitudinally aligned, the sheath 700 travels along the barrel and a greater rate than the travel of the plunger 750.

FIG. 8c shows the apparatus with the sheath 700 fully deployed. The rotators 774a-b are configured to ride over the first hinged section during and after rotation thereof. When the sheath 700 is fully deployed, the hinged sections of the lever arms 770a-b are substantially aligned along a length of the syringe and/or apparatus. The sheath 700 is locked in place by the rotators 774a-b. This lock is provided by the rotators 774a-b overlapping the lever arms 770a-b when the sheath 700 is fully deployed. The overlapping prevents the lever arms 770a-b from rotating and therefore locks the sheath 700 in place.

Figure 9:
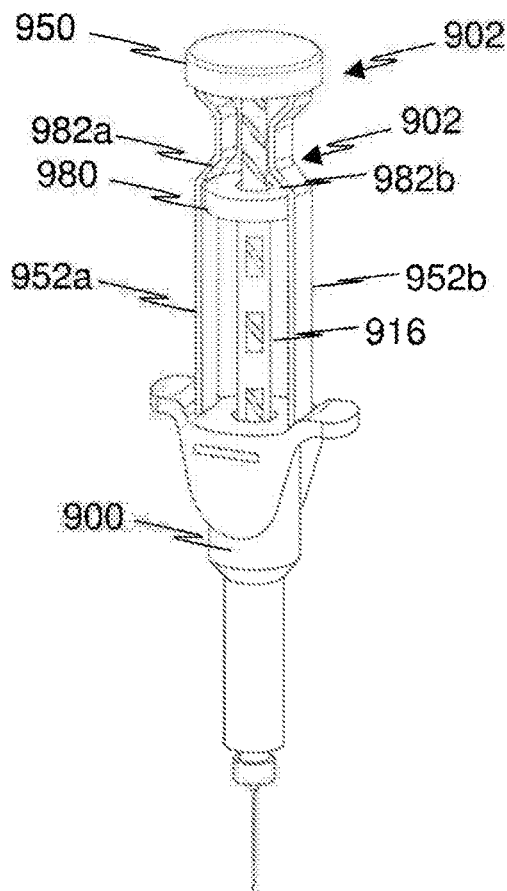
FIG. 9 is a perspective view of an exemplary apparatus fitted to a syringe for providing a safety syringe.

FIG. 9 shows an exemplary safety syringe apparatus fitted to a syringe. Some of the features of the apparatus of FIG. 9 are the same or similar to corresponding features of the apparatus of any of FIGS. 1, 3, 5 and 7 and may have the same or a similar purpose. As such, these features are not described again in detail here. Similar reference numerals may be used for similar features, except prefixed by a "9".

The exemplary apparatus of FIG. 9 comprises a sheath 900 and a sheath actuator 902. The sheath actuator 902 comprises a safety plunger 950 that is coupled to a syringe plunger 916 and configured to decouple from the syringe plunger 916 at a point on the stroke. There are a number of ways that such decoupling may occur and one way is as described with reference to FIGS. 5, 6a-c, 7 and 8a-c above.

The sheath 900 is coupled to the safety plunger by legs 952a-b. The legs 952a-b are bent and configured such that they may be straightened to increase an extension of the sheath 900. That is, the bent legs 952a-b are configured to provide a ratioed mechanism 904 to ensure a greater magnitude of movement of the sheath 900 than a magnitude of movement of the safety plunger 950.

In the exemplary apparatus of FIG. 9, the legs 952a-b are bent laterally inwards to form a deviation in the path of the legs 952a-b. The syringe plunger comprises a straightening member 980 that is in the exemplary form of a disc. The disc 980 is positioned at a point below (i.e. inward, in terms of the safety plunger stroke) the bends in the legs 952a-b. The disc 980 is arranged to interact with reaction surfaces 982a-b formed by the bends in the legs 952a-b for straightening the legs 952a-b.

Referring to FIG. 10a, when a force 964 is applied by a user to the safety plunger 950, the syringe plunger 916 and the sheath 900 also move in the same direction due to the coupling between them. At a point on the stroke of the syringe plunger 916, it becomes decoupled from the safety plunger 950 by some means, including those described above. As shown in FIG. 10a', on continued motion of the safety plunger 950, the syringe plunger 916 begins to rotate as shown by arrow 984 under a force exerted by reciprocal threaded portions on the syringe plunger 916 and the safety plunger 950. Linear motion of the safety plunger 950 continues and the straightening means 980 interacts with the reaction surfaces 982a-b to straighten the legs 952a-b causing ratioed deployment of the sheath 900 by increasing the extension of the legs 952a-b, as shown by arrows 986a-b.

FIG. 10b shows the apparatus with the sheath 900 fully deployed and the legs 952a-b straightened, as shown in FIG. 10b'.

Figure 11:
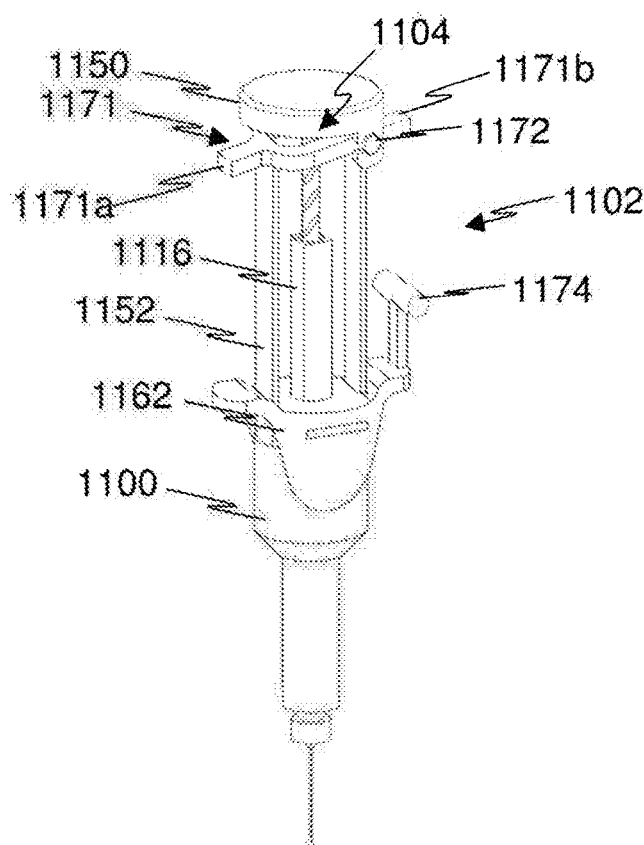
FIG. 11 is a perspective view of an exemplary apparatus fitted to a syringe for providing a safety syringe.

FIG. 11 shows an exemplary apparatus fitted to a syringe for providing a safety syringe. Some of the features of the apparatus of FIG. 11 are the same or similar to corresponding features of the apparatus of any of FIGS. 1, 3, 5, 7 and 9 and may have the same or a similar purpose. As such, these features are not described again in detail here. Similar reference numerals may be used for similar or the same features, except prefixed by a "11".

The exemplary apparatus of FIG. 11 comprises a sheath 1100 and a sheath actuator 1102. The sheath actuator 1102 comprises a safety plunger 1150 that is coupled to a syringe plunger 1116 and configured to decouple from the syringe plunger 1116 at a point on the stroke. There are a number of ways that such decoupling may occur and one way is as described with reference to FIGS. 5, 6a-c, 9 and 10a-b above.

The sheath 1100 is coupled to the safety plunger by one or more legs 1152. The leg 1152 may not be locked to the sheath 1100 and may be coupled thereto, such that an inward stroke of the safety plunger 1150 causes movement of the sheath 1100 in the same direction, but an outward stroke of the safety plunger 1150 does not cause any movement of the sheath 1100. Alternatively, the leg 1152 may be connected to the sheath 1100.

The apparatus further comprises a lever arm 1171. The lever arm 1171 provides a ratioed mechanism 1104 for deployment of the sheath 1100. A first end of the lever arm 1172 is rotatably connected to the safety plunger 1150 at a point 1172 that is fixed with respect to the safety plunger and/or movable relative to the syringe after decoupling of the safety plunger 1150 from the syringe plunger 1116. A second end of the lever arm 1171 is connected to the sheath 1100 via the leg 1152. That is, the connection between the lever arm 1150 and the sheath 1100 is indirect. The lever arm 1171 is configured such that rotation thereof moves the leg 1152 longitudinally. The leg 1152 is coupled to the sheath 1100 such that longitudinal movement of the leg 1152 causes extension of the sheath 1100. The lever arm 1171 may comprise a plurality of hinged sections and/or may be directly connected to the sheath 1100.

The syringe comprises a rotator 1174 that is configured to rotate the lever arm 1171 after decoupling of the safety plunger 1150 from the syringe plunger 1116. In the exemplary apparatus of FIG. 11, the rotator 1174 comprises a projection from a handle portion 1162 in a direction of the safety plunger 1150. In the exemplary apparatus of FIG. 11, the lever arm 1171 comprises a first end 1171a and second end 1171b, each extending from the point of rotation 1172. The second end 1171b is shorter than the first end 1171a to provide the ratioed mechanism. The rotator 1174 is configured to engage the second end 1171b to rotate the lever arm 1171.

Figure 12A:
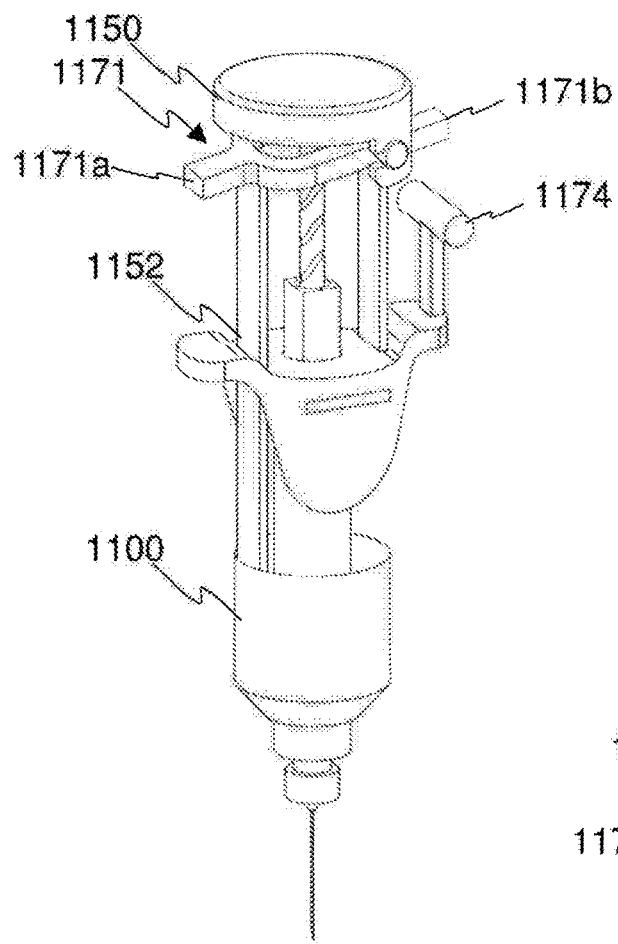
FIGS. 12a-b show stages of operation of an exemplary apparatus fitted to a syringe for providing a safety syringe.
Figure 12B:
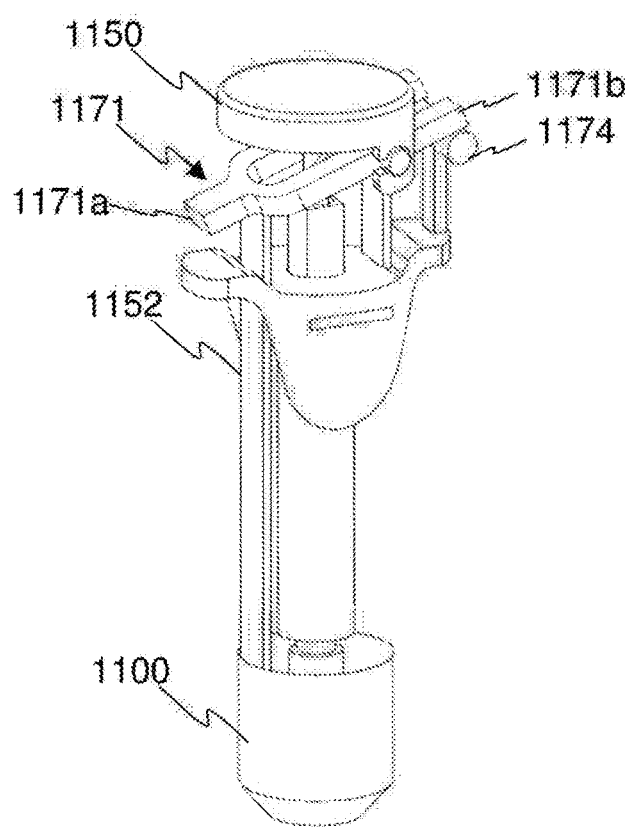

FIGS. 12a-b show various stages of use of the apparatus of FIG. 11. When a force is applied by a user to depress the safety plunger 1150, movement of the syringe plunger 1116 is caused due to the coupling between the two. At a point on the stroke of the safety plunger 1150, it decouples from the syringe plunger 1116. In exemplary arrangements, the decoupling may be as explained above with reference to other exemplary apparatus.

After decoupling, continued movement of the safety plunger 1150 brings the second end 1171b of the lever arm 1171 into contact with the rotator 1174. Further movement of the syringe plunger 1150 causes rotation of the second end 1171b, which results in a corresponding rotation of the first end 1171a about the pivot point 1172. Because they are at opposed sides of the pivot point 1172, upward movement of the second end 1171b causes downward movement of the first end 117a. A ratioed rotation of the first end 1171a is caused by the relative lengths of the first and second ends 1171a, b. Rotation of the first end 1171a causes longitudinal movement of the leg 1152, which deploys the sheath 1100.

Figure 13A:
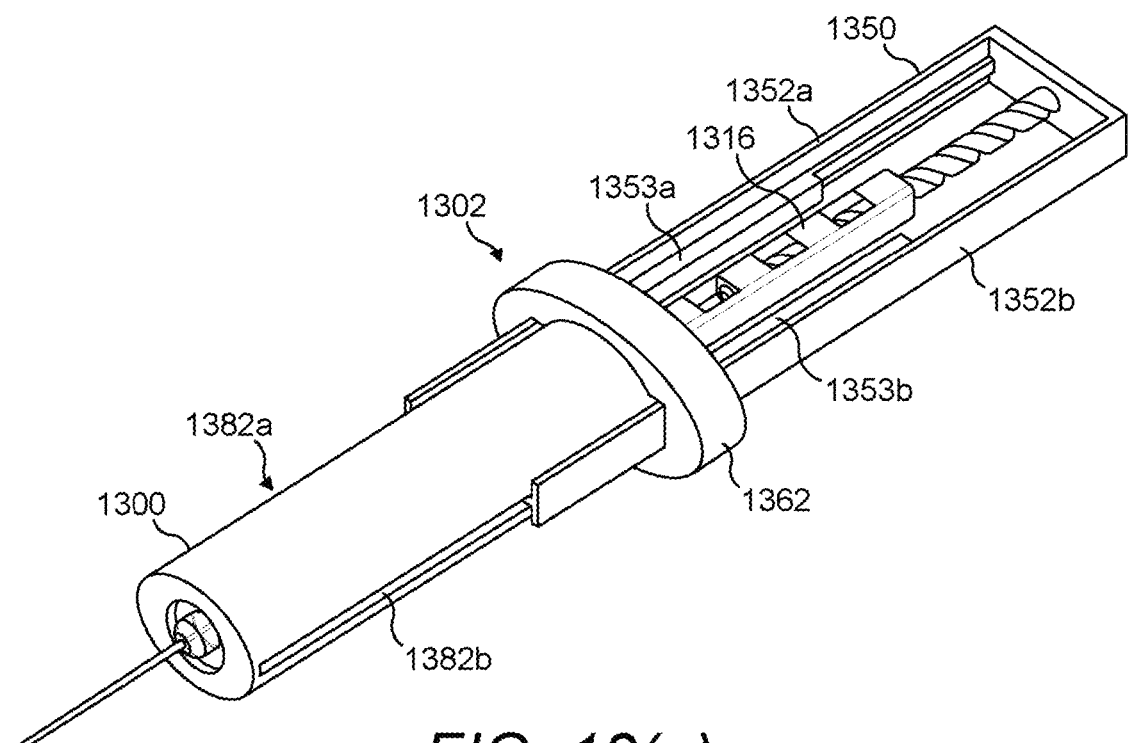
FIGS. 13a and 13b are perspective views of an exemplary apparatus fitted to a syringe for providing a safety syringe.
Figure 13B:
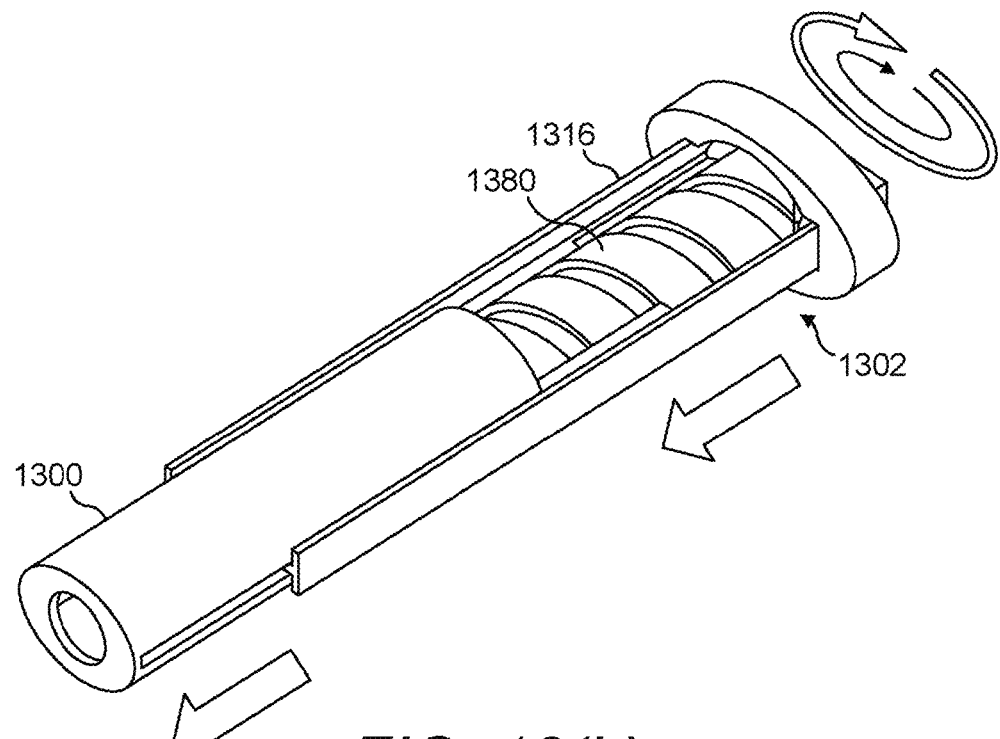

FIGS. 13a and 13b show an exemplary apparatus fitted to a syringe for providing a safety syringe. FIG. 13a shows the apparatus before use and FIG. 13b shows the apparatus during use at a point in which a mount is visible. Some of the features of the apparatus of FIGS. 13a and 13b are the same or similar to corresponding features of the apparatus of any of FIGS. 1,3, 5, 7, 9 and 11 and may have the same or a similar purpose. As such, these features are not described again in detail here. Similar reference numerals may be used for similar or the same features, except prefixed by a "13".

The exemplary apparatus of FIG. 13 comprises a sheath 1300 and a sheath actuator 1302. The sheath actuator 1302 comprises a safety plunger 1350 that is coupled to a syringe plunger 1316 and configured to decouple from the syringe plunger 1316 at a point on the inward stroke. There are a number of ways that such decoupling may occur, as described below and with reference to FIGS. 5, 6a-c, 9, 10a-b, 11 and 12a-b above.

The sheath actuator 1302 of the exemplary apparatus of FIGS. 13a and 13b also comprises a mount 1380, which provides a threaded linkage between the sheath and the sheath actuator and is visible in FIG. 13b. The mount 1380 is configured to act as a lead screw for translating rotary motion of the mount 1380 into linear motion of the sheath 1300, as explained below. The mount 1380 cooperates with corresponding features, for example a corresponding thread, of the sheath 1300 to translate rotational motion of the mount 1380 into linear motion of the sheath 1300. Specifically, the mount 1380 comprises a helical guide configured to interact with corresponding features on the sheath 1300.

The safety plunger 1350 comprises a head and a plurality (two in the exemplary apparatus of FIG. 13) of legs 1352a, b extending towards the sheath 1300. The sheath 1300 comprises guide channels 1382a, b into which a corresponding feature of the legs 1352a, b are received. The guide channels 1382a, b allow relative linear movement of the sheath 1300 and the legs 1352a, b.

In the exemplary apparatus of FIGS. 13a and 13b, the safety plunger 1350 is coupled to the syringe plunger 1316 at a start point of the inward stroke. In the exemplary apparatus of FIGS. 13a and 13b, the coupling is provided by interaction between the legs 1352a, b of the safety plunger 1350 and corresponding features on the mount 1380. The threaded portion of the safety plunger 1350 comprises a further helical guide that exerts a rotational force on the syringe plunger 1316, but the syringe plunger 1316 is prevented from rotating along at least part of its stroke by the interaction between the legs 1352a, b of the safety plunger 1350 and corresponding features on the mount 1380 such that linear coupling is provided. The legs 1352a, b and the mount 1380 may be configured to prevent rotation of the mount 1380 until the correct point on the inward stroke of the safety plunger 1350. This in turn provides linear coupling between the safety plunger 1350 and the syringe plunger 1316 because the syringe plunger 1316 is rotationally coupled to the mount 1380 and so is not free to rotate. In the exemplary apparatus of FIGS. 13a and 13b, ribs 1353a, b on the legs 1352a, b are configured to be received in slots in a lip of the mount 1380 (shown in FIG. 14b) to prevent rotation of the mount. The ribs 1353a, b do not extend along the entire length of the legs 1352a, b and an upper portion of each leg 1352a, b has no rib 1353a, b. Therefore, once the ribs 1353a, b have passed through the slots, the mount 1380 is free to rotate and the syringe plunger 1316 is no longer linearly coupled to the safety plunger 1350. Continued movement of the safety plunger 1350 therefore causes the threaded portion of the safety plunger 1350 to rotate the syringe plunger 1316, which is rotationally coupled to the mount 1380, which therefore also rotates.

In alternative arrangements, linear decoupling may be provided by a combination of a threaded portion of the safety plunger 1350 and a keyed entry of the syringe plunger 1316 into the barrel of the syringe, as described above in relation to other apparatus.

In such arrangements, rotation is prevented by a non-circular cross sectional shape of the syringe plunger 1316 interacting with a corresponding aperture at the entrance to the barrel. The corresponding aperture may be in a handle portion 1362 that is fixed in relation to the barrel of the syringe. The syringe plunger 1316 is configured to be rotatable at a point on the stroke, such that the safety plunger 1350 and the syringe plunger become decoupled, that is, linear motion of the safety plunger 1350 need not result in linear motion of the syringe plunger 1316. After that, rotation of the mount 1380 is possible.

As shown better in FIGS. 14a-d, the cross sectional shape of the syringe plunger 1316 is configured to rotationally couple the syringe plunger 1316 to the mount 1380. After linear decoupling of the safety plunger 1350 and syringe plunger 1316, the mount 1380 is rotatable with respect to the sheath 1300 and the safety plunger 1350. Further, the mount 1380 is configured to be rotatable relative to barrel of the syringe. As the safety plunger 1350 exerts a rotational force on the syringe plunger 1316 and the syringe plunger 1316 is rotationally coupled to the mount 1380 after decoupling of the safety plunger 1350 and the syringe plunger 1316, further movement of the safety plunger 1350 causes rotation of the syringe plunger 1316 and the mount 1380 under the force exerted by the further helical guide.

Referring to FIGS. 14a-d, the operation of the apparatus of FIGS. 13a and 13b is shown. FIG. 14a shows the apparatus before use. The safety plunger 1350 is coupled to the syringe plunger 1316 such that linear motion of the safety plunger 1350 results in linear motion of the syringe plunger 1316. The coupling is provided by the further helical guide of the safety plunger 1350 interacting with corresponding features of the syringe plunger 1316 and the fact that rotation of the mount 1380 is prevented by the ribs 1353a, b interacting with slots in the lip (shown in FIG. 14b) of the mount 1380. The syringe plunger 1316 is also rotationally coupled to the mount 1380 such that rotation of the syringe plunger 1316 results in rotation of the mount 1380.

In FIG. 14b, a force is applied by a user to the head of the safety plunger 1350, as shown by arrow 1364. The safety plunger 1350 has moved to a point where the ribs 1353a, b have moved below the lip 1381 of the mount 1380 and no longer prevent its rotation. This point in the exemplary apparatus is at the end of the inward stroke of the syringe plunger 1316, when the plunger has reached the bottom of the barrel. In the exemplary apparatus, the syringe plunger 1316 is now able to rotate because it is rotationally coupled to the mount 1380, which is now able to rotate.

As shown in FIG. 14c, continued movement of the safety plunger 1350 rotates the syringe plunger 1316 due to the interaction between the further helical guide of the safety plunger 1350 and the corresponding features of the syringe plunger 1316. Rotation of the syringe plunger 1316 causes rotation of the mount 1380, as shown by arrows 1386 and 1388 respectively. Because the mount 1380 acts as a lead screw, rotation thereof causes extension of the sheath 1300 due to the interaction between the helical guide of the mount and the corresponding features of the sheath 1300. The helical guide of the mount 1380 may be configured to provide a ratioed mechanism for deployment of the sheath 1380. This may be done by increasing an angle of the helical guide such that it is greater than the angle of the further helical guide of threaded portion of the safety plunger 1350. In this way the magnitude of linear motion of the sheath 1300 is greater than the magnitude of the linear motion of the safety plunger 1350 after decoupling.

FIG. 14d show a fully deployed sheath 1300 that is at least partially covering the needle. The continued movement of the safety plunger 1350 results in the continued rotation of the mount 1380 and the syringe plunger 1316, as shown by the arrows 1386 and 1388 respectively. The rotation of those members results in the continued extension of the sheath 1350.

The skilled person will be able to envisage other embodiments without departing from the scope of the appended claims.

The invention claimed is:

1. An apparatus for use with a syringe to provide a safety syringe, the apparatus comprising:
 a sheath deployable to at least partially cover a needle of the syringe;
 a sheath actuator to deploy the sheath; and
 a ratioed mechanism comprising a rack and pinion arrangement linking the sheath and the sheath actuator and configured such that a magnitude of movement of the sheath is greater than a magnitude of movement of the sheath actuator during deployment of the sheath.

2. An apparatus according to claim 1, wherein the sheath actuator is operable on in-line movement thereof.

3. An apparatus according to claim 2, wherein the sheath actuator comprises a plunger and a handle portion configured to deploy the sheath by relative movement between the plunger and the handle portion.

4. An apparatus according to claim 1, wherein the ratioed mechanism comprises a pinion engaged with a first rack connected to the sheath actuator and a second rack connected to the sheath.

5. An apparatus according to claim 4, wherein the pinion comprises a first set of teeth engaged with the first rack and a second set of teeth engaged with the second rack, and wherein the first set of teeth has a smaller radius than the second set of teeth.

6. A safety syringe comprising a syringe and an apparatus according to claim 1.

* * * * *